United States Patent [19]
Crowley et al.

[11] Patent Number: 5,313,944
[45] Date of Patent: May 24, 1994

[54] MEASUREMENT OF INTERNAL BODY STRUCTURE DURING BIOMAGNETOMETRY

[75] Inventors: Christopher Crowley, San Diego; D. Scott Buchanan, Escondido; Waldo S. Hinshaw, Burlingame, all of Calif.

[73] Assignee: Biomagnetic Technologies, Inc., San Diego, Calif.

[21] Appl. No.: 948,386

[22] Filed: Sep. 21, 1992

[51] Int. Cl.$^5$ .............................................. A61B 5/05
[52] U.S. Cl. .............................. 128/653.1; 128/661.03
[58] Field of Search ................ 128/653.1, 731, 661.03, 128/661.05; 324/244, 248, 260

[56] References Cited

U.S. PATENT DOCUMENTS 4,793,355 12/1988 Crum et al. ......................... 128/713
4,971,060 11/1990 Schneider et al. ................ 128/653.1
5,152,288 10/1992 Hoenig et al. .................... 128/653.1

Primary Examiner—Ruth S. Smith
Attorney, Agent, or Firm—Gregory Garmong

[57] ABSTRACT

A biomagnetometer measures a magnetic field produced by a source within the body of a subject, using a magnetic field sensor system. The biomagnetometer includes an ultrasonic transceiver that determines the internal physical structure of the body with ultrasonic waves. An electromagnetic transmitter/receiver establishes the position of the ultrasonic transceiver relative to the magnetic field sensor system. A computer controls and integrates the magnetic field sensor system, the ultrasonic transceiver, and the electromagnetic transmitter/receiver. The biomagnetometer permits a direct association between the measured biomagnetic field and the location of the source within the body of the subject.

18 Claims, 2 Drawing Sheets

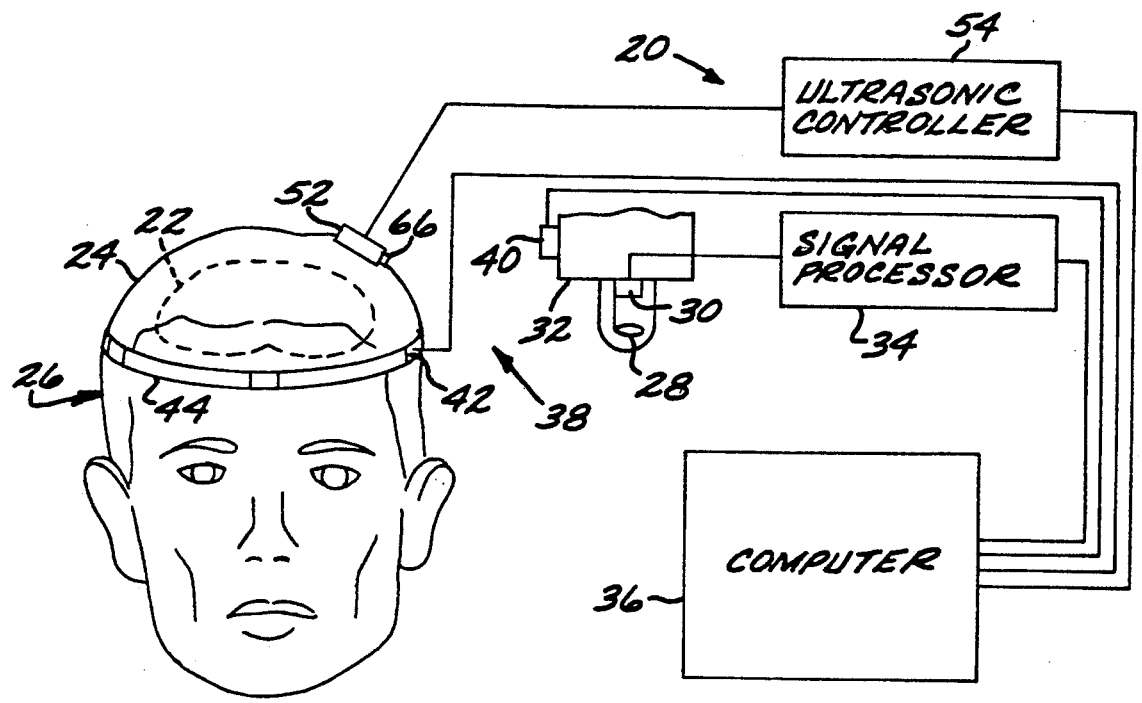
FIG.1
FIG.2
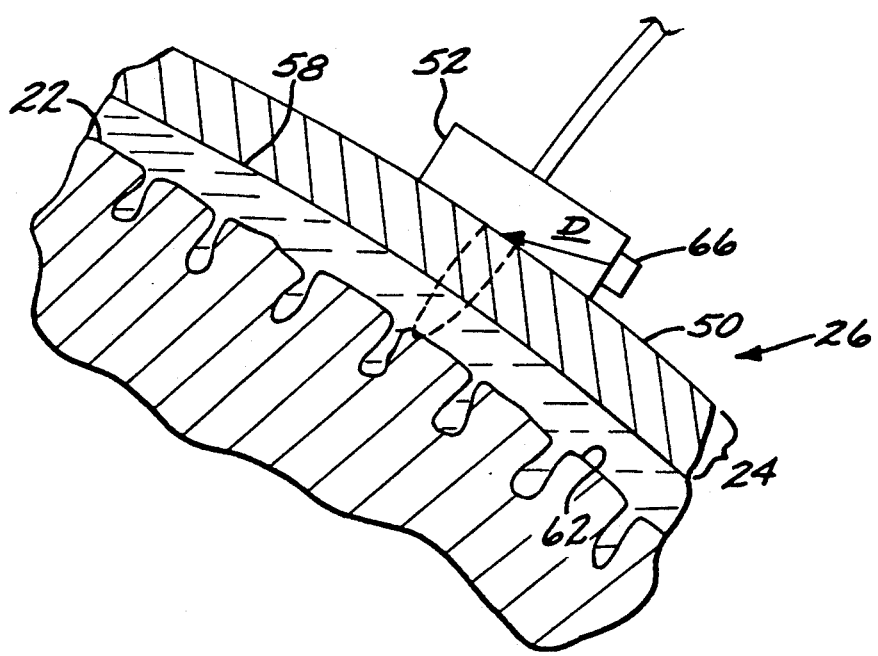

MEASUREMENT OF INTERNAL BODY STRUCTURE DURING BIOMAGNETOMETRY

BACKGROUND OF THE INVENTION

This invention relates to the measurement of magnetic fields produced by the human body, and, more particularly, to a biomagnetometer that permits automated correlation of magnetic field measurements with the source of the magnetic field within the body of the subject.

Organs within the human body, most notably the brain, the heart, and the nerves, generate or conduct electrical signals. These electrical signals in turn produce magnetic fields that may be measured by an instrument positioned externally to the body. Such an instrument, termed a biomagnetometer, includes a sensitive detector of very weak magnetic fields, since the magnetic field emitted by the brain, for example, is on the order of one-ten millionth of the magnitude of the earth's magnetic field.

As the technology of biomagnetometry advances, doctors and researchers are discovering correlations between the magnetic activity of the body and its state of health, and are also gaining an understanding of cognitive processes and other functions of the body. A primary application of the technology is deducing from the measured external magnetic fields the location and nature of the electric currents which were the sources of the fields. Both functional and dysfunctional portions of organs can be identified in this manner.

It is important that the magnetic field be measured correctly, and that the origin of the magnetic field be determined accurately from the measurement. The biomagnetometer must be capable of making accurate local magnetic field measurements external to the body and then utilizing those measurements in conjunction with geometric information about the body being measured and the measurement system to identify the operating electrical and magnetic field sources within the body and their location.

Local magnetic field measurements are made with biomagnetometers, which utilize sensitive detector systems having magnetic field pickup coils and Superconducting QUantum Interference Device (SQUID) detectors. Such systems, which are capable of measuring very small magnetic fields, also include sophisticated signal processing instrumentation that can isolate the measured magnetic field of interest from spurious fields produced by other sources and that are detected simultaneously. Such biomagnetometers are commercially available from Biomagnetic Technologies, Inc., San Diego, Calif.

An important advance in correlating the measured magnetic field with its precise origin in the body is disclosed in U.S. Pat. No. 4,793,355, which describes an electromagnetic transmitter/receiver system for automatically measuring the location of the body relative to the magnetic field detector. The position of the body is recorded along with the measured magnetic field. Thus, for example, the actual position of the head may be measured and continuously recorded at the same time as the magnetic fields produced by the brain are measured and recorded. If the subject's head moves slightly during the course of a magnetic field measurement, the correlation between magnetic field measurement and head position is still maintained. In prior approaches, the subject's head had to be restrained to a preestablished position during the measurements, and the restraint in itself could result in spurious magnetic field signals. A commercial version of the apparatus disclosed in U.S. Pat. No. 4,793,355 is also available from Biomagnetic Technologies, Inc., for use in conjunction with its biomagnetometers.

There remains the problem of correlating the measured magnetic field with the location and shape of its source organ within the body. An illustration drawn from the problem of most practical interest is helpful in understanding the significance of this problem. The brain is located within the skull of the subject. The thickness of the skull varies from location to location around the head, so that the brain is not located at some uniform depth below the surface of the skull. The existing biomagnetometers can make accurate measurements of the magnetic field produced by the brain at locations outside the skull, and can correlate those measurements to the skull location using the approach disclosed in the '355 patent.

However, the existing biomagnetometers cannot determine the shape of the interior surface of the skull and directly associate the measured magnetic field with a location within the brain—only to a location within the skull. Knowledge of the shape of the interior surface of the skull is also important in performing inverse calculations of the nature of the source from the external magnetic fields. Since there is an electrically conductive region that follows the interior surface of the skull, the skull can influence the measured external magnetic field produced by a source within the brain.

Knowledge of the location of the brain within the skull permits the physiological correlation of electrical signal and physical source that is the ultimate objective of the system. In the existing approaches, the shape of the interior surface of the skull and the location of the brain within the skull must be assumed from a model of the head, or provided by other measurements such as an X-ray of the head. After the magnetic field measurements are performed, an X-ray of the head can be used to correlate the position and shape of the brain with the position and shape of the skull. Such approaches are inaccurate, in the case of the assumption of a head structure, or imprecise and awkward to use, in the case of X-rays or the like.

There is a need for direct correlation of the position and shape of the source organ, such as the brain, and intervening electrically conductive structure, such as the skull, with the measured magnetic field. The greatest need is experienced in the area of brain measurements, because the magnitude of the magnetic fields is small and must be known accurately, because of the high required spatial accuracy of the correlations, and because of the presence of the skull around the brain. However, the need appears in relation to other biomagnetic measurements as well. The present invention fulfills this need, and further provides related advantages.

SUMMARY OF THE INVENTION

The present invention provides a biomagnetometer in which magnetic field measurement, body location, and source organ and conductive interface positions and shapes are automatically recorded and made available for accurate magnetic field source determinations. Laborious and often erroneous correlations of data taken by different techniques are avoided, and all data can be coordinated automatically into a uniform coordinate frame of reference. The approach of the invention is readily integrated with the technology of existing advanced biomagnetometers, both physically and in an instrumentation sense.

In accordance with the invention, a biomagnetometer measures a magnetic field produced by a source organ within the body of a subject and correlates that field with the internal structure of the body. The biomagnetometer comprises means for measuring a magnetic field produced by a source organ and means for determining the internal structure of the body relative to the means for determining, both the means for measuring and the means for determining being external to the body. A computer controls the means for measuring and the means for determining. Preferably, there is also means for establishing the location of the means for determining relative to the location of the means for measuring, including, for example, an electromagnetic transmitter and an electromagnetic receiver. One of the transmitter and the receiver is located on the means for determining and the other is located at a known location relative to the means for measuring. Thus, the location and shape of the source organ can be determined relative to the means for measuring the magnetic field, so that correlations of the measured magnetic field and the internal physical structure of the body can be made.

The means for determining is preferably an ultrasonic transceiver that directs an ultrasonic wave into the body at a selected location, and receives a reflected wave back from the internal structure of the body at substantially the same location. The distance to an underlying structure is computed from the time of flight of the ultrasonic wave to travel to the structure. For example, the inside surface of the skull produces a reflected ultrasonic wave which is received back at the transceiver. The thickness of the skull is determined as one-half (because the wave travels through the thickness of the skull twice) of the product of the velocity of the wave through skull bone (a known constant quantity, which is typically about 3000 meters per second) and the measured time between the transmitting of the ultrasonic wave and the receipt of the reflected wave. This information is automatically gathered and stored in the control computer as each measurement is taken.

The location of the ultrasonic transceiver, at the time of making a measurement such as the skull thickness measurement, is preferably recorded using the positioning system described in U.S. Pat. No. 4,793,355, whose disclosure is incorporated by reference. Either an electromagnetic transmitter or receiver is fixed to the ultrasonic transducer, with the corresponding receiver or transmitter fixed in some known location with respect to the means for measuring the magnetic field. The position of the ultrasonic transceiver with respect to the head or other part of the body being measured is then recorded automatically as the thickness measurement is made. A map of source organ location and, in the case of the head, the skull thickness as a function of location on the head, is developed and stored. This mapping is preferably conducted before the taking of magnetic field data begins, so that the measured magnetic field data can be interpreted accurately in real time using the local skull thickness from the stored map. The precise locations of the sources of the measured magnetic field within the source organ may be calculated using this same information.

The present invention provides an important advance in the art of biomagnetometry. The actual position and shape of internal organs, and the thickness of overlying structure such as the skull, can be determined in the same coordinate positional system as the biomagnetic measurements are taken, and automatically supplied to the data processing computer. Models based upon assumptions such as a brain centered within a skull of constant known thickness, which are known to be only approximations, need no longer be used. The accuracy of measurements of the intensity and spatial origin of magnetic fields produced by the body can therefore be improved. Other features and advantages of the invention will be apparent from the following more detailed description of the preferred embodiments, taken in conjunction with the accompanying drawings, which illustrate, by way of example, the principles of the invention.

BRIEF DESCRIPTION OF THE DRAWINGS

FIG. 1 is a schematic view of a biomagnetometer and its instrumentation, in relation to a human skull containing a brain whose magnetic field is be measured;

FIG. 2 is an enlarged sectional view of the skull of FIG. 1, showing the relation of the ultrasonic transceiver to the skull during a measurement of skull thickness;

DETAILED DESCRIPTION OF THE PREFERRED EMBODIMENTS

Figure 3:
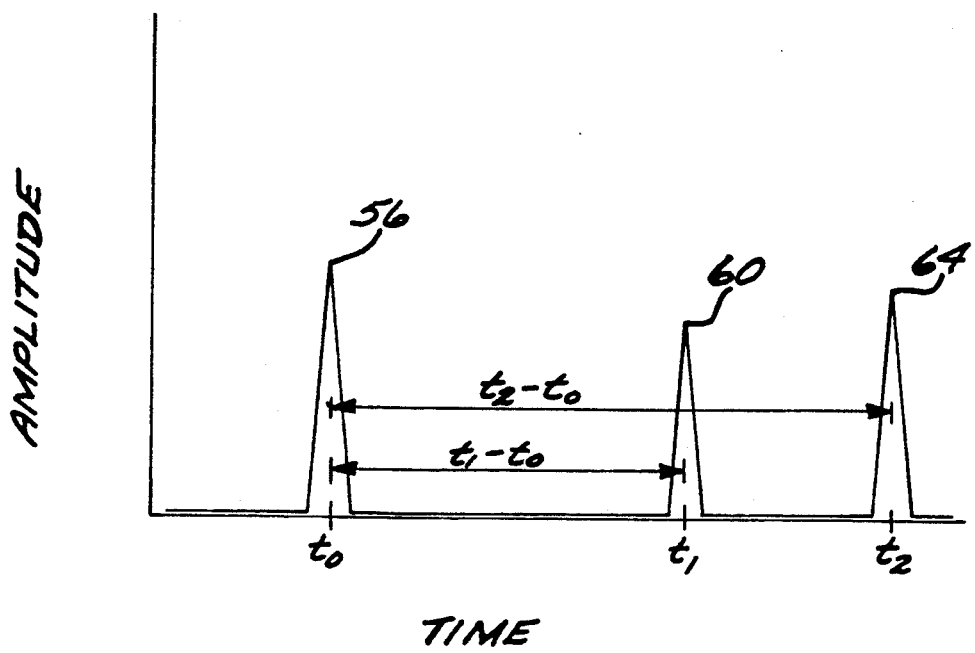
FIG. 3 is a graph of ultrasonic wave amplitude as a function of time.

In accordance with a preferred embodiment of the invention, a biomagnetometer that measures a magnetic field produced within a body of a subject comprises means for measuring a magnetic field, the means for measuring being external to a body of a subject, and an ultrasonic transceiver system that transmits an ultrasonic wave into the body of the subject at a selected location on the body and receives a reflected ultrasonic wave from the interior of the body of the subject. The biomagnetometer further includes means for establishing the position of the ultrasonic transceiver system relative to the means for measuring, preferably including an electromagnetic transmitter/receiver means for establishing the position of the ultrasonic transceiver system relative to the means for measuring. The electromagnetic transmitter/receiver means includes an electromagnetic transmitter and an electromagnetic receiver, one of the transmitter and the receiver being located on the ultrasonic transceiver and the other being located at a known location relative to the means for measuring.

As illustrated in FIG. 1, a biomagnetometer 20 is used to perform measurements of the magnetic field produced by a brain 22 located within a skull 24 of a subject 26. The biomagnetometer 20 includes a flux-measuring pickup coil 28 in which an electrical current is generated when magnetic flux passes through the pickup coil 28. The pickup coil can be a single turn coil, a gradiometer, or any other type of flux measuring device. The electrical current produced by the coil is detected by a Superconducting QUantum Interference Device (SQUID) 30. The coil 28 and SQUID 30 are operated within a cryogenic dewar 32. The signal of the SQUID is processed through signal processor 34, whose output is stored in a computer 36. This aspect of a biomagnetometer is well known, and commercial units are available. See also U.S. Pat. Nos. 4,793,355; 3,980,076; 4,389,612; 4,079,730; 4,386,361; and 4,403,189, whose disclosures are incorporated by reference.

A two-step method is used to establish the precise location and shape of the organ (in this case the brain 22 and its surrounding fluid) from which the magnetic field emanates, relative to the means for measuring the magnetic field (in this case the pickup coil 28). In one step, the location of the external surface of the body is established, preferably using a known approach. In the other step, the internal structure of the body relative to the external surface of the body is determined. These two steps are preferably accomplished simultaneously.

In the first step, and referring to FIG. 1, the location of the external surface of the skull 24 with respect to the biomagnetometer 20 is determined using an electromagnetic positioning system 38. The positioning system 38 includes electromagnetic transmitters and receivers, one of which is fixed in respect to the skull 24 and the other of which is fixed in respect to the pickup coil 28. For definiteness in illustration, in FIG. 1 a transmitter 40 is fixed onto the side of the dewar 32, and a receiver 42 is fixed in relation to the skull 24 of the subject 26, as with an elastic headband 44 or other means such as an adhesive. Signals from the transmitter 40 and receiver 42 are conveyed to the computer 36, as a measure of the position of the skull with respect to the dewar. The position of the transmitter 40 with respect to the pickup coil 28 is fixed and known, and is determined during the construction and calibration of the dewar 32. The discussion of the positioning system presented in this paragraph is brief, and does not cover all of the details of apparatus arrangement and instrumentation. Full details of this positioning system 38, as well as its operation, are set forth in U.S. Pat. No. 4,793,355, whose disclosure is incorporated by reference.

In the second step, and referring to FIG. 2, the skull 24 is formed of a bony material and has a thickness that is typically on the order of from about 0.5 to about 2 centimeters, varying over the surface of the head for each individual, and from individual to individual. The brain 22 is supported within the skull 24. An important advantage of biomagnetometry is that it is noninvasive. Therefore, there is access only to an outer surface 50 of the skull 24.

The internal structure within the head of the subject 26, including the shape and position of the brain, the thickness of the skull, and other relevant structure, relative to the outer surface of the skull are preferably determined using an ultrasonic technique. An ultrasonic transducer 52 is contacted to the outer surface 50 of the skull 24. The transducer 52 is preferably operated both to send and receive ultrasonic signals, and in this operational mode is termed a "transceiver". Equivalently, separate ultrasonic transmitters and receivers can be used. The ultrasonic signal, which typically is on the order of 5 MHz (megahertz) frequency, is coupled into the head of the subject 26 either with a pressure contact or with a couplant such as grease spread over the area to be measured. The operation of the transducer 52 is controlled by an ultrasonic controller 54. Ultrasonic transducers 52 and controllers 54 are available commercially and widely used in other applications.

The skull 24 has a thickness that varies according to the position selected for the measurement. The local thickness is determined from the time of flight of the ultrasonic wave through the skull material. FIG. 3 is a graph of ultrasonic amplitude as measured at the ultrasonic controller 54 as a function of time. An initial peak 56 at time to is an ultrasonic signal transmitted into the skull 24 by the transducer 52. A portion of the energy of the transmitted signal is reflected from an inner surface 58 of the skull 24, and is received back at the transducer 52 as a peak 60 at time t1-to. Another portion of the energy of the transmitted signal is reflected from an outer surface 62 of the brain 22, and is received back at the transducer 52 as a peak 64 at time t2-to.

The distance from the transducer 52 (located in close contact to the outer surface 50 of the skull) to the inner surface 58 of the skull 24, the thickness Ts of the skull 24, is $$Ts = \tfrac{1}{2}(Vs)(t1\text{-}to)$$

where Vs is the velocity of an ultrasonic wave in the bony material of the skull, which is a constant equal to about 3000 meters per second. The distance Db to the outer surface 62 of the brain is $$Db = Ts + \tfrac{1}{2}(Vf)(t2\text{-}t1)$$

where Vf is the velocity of an ultrasonic wave in the fluid in which the brain is suspended, which is a constant equal to about 1500 meters per second. The values of to, t1, and t2 (or equivalently, their differences), are determined by the ultrasonic controller 54, and provided to the computer 36. The computer determines Ts and Db values from this measured information and the constant values of Vs and Vf, which are provided as input values to the computer.

Some typical measured values of Ts range from about 0.5 to about 1.5 centimeters, and some typical measured values of Db range from about 1 to about 2 centimeters.

The values of Ts and Db vary from location to location on the head of any one individual. To form a complete mapping of these values on the head of any one subject, it is necessary to associate each pair of (Ts, Db) values with a location on the head of the subject. To be of value in the biomagnetometry analysis, the location information should be in the same frame of reference with respect to the coil 28 as are the measurements taken by the positioning system 38.

To associate a unique position value with each measurement of skull thickness and distance to the brain, an electromagnetic transmitter or receiver is fixed to the ultrasonic transducer 52. The selection of transmitter or receiver is made to correspond to the previously selected configuration of the positioning system 38. In the preferred system illustrated in FIG. 1, an electromagnetic receiver 42 is fixed to the skull 24. An electromagnetic receiver 66 is therefore fixed to the ultrasonic transducer 52, as on its side in the manner illustrated in FIG. 2. The outer surface 50 of the skull 24 is located at a vector location D with respect to the receiver 66, which vector D is determined by measuring the assembly of transducer 52 and receiver 66.

Figure 4:
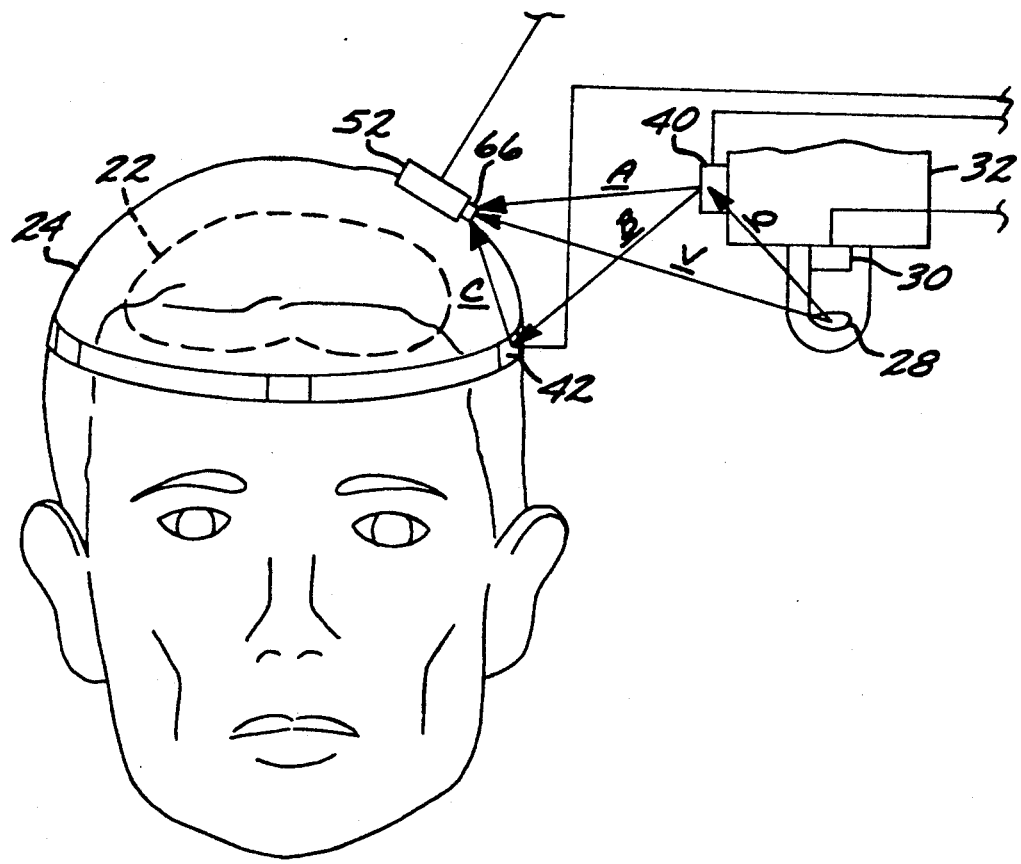
FIG. 4 is an enlarged front schematic elevational view of the skull of FIG. 1, with a measurement frame of reference.

The receiver 66 is of the same type as the receiver 42, and its position relative to the transmitter 40 is determined in the same fashion as the position of the receiver 42 relative to the transmitter 40. This approach is described in the '355 patent. The position of the receiver 66 relative to the transmitter 40 is illustrated in FIG. 4 as vector A, and the position of the receiver 42 relative to the transmitter 40 is illustrated as a vector B. Also in FIG. 4, the position of the transmitter 40 relative to the coil 28, where the magnetic field is actually measured, is illustrated as a vector O, and the position of the receiver 66 relative to the receiver 42 is illustrated by a vector C. A vector V+D from the coil 28 to the outer surface 50 of the skull 24 is a principal vector of interest, because it enables a skull thickness measurement or brain position measurement at that particular position to be used in biomagnetometric analysis and corrections.

By a direct vector addition, $$V = O + B + C.$$

The outer surface of the skull is located, relative to the pickup coil 28, at $$V + D = O + B + C + D.$$

Vectors O, C, and D are fixed values for any particular series of measurements, with O and D being fixed by the construction of the dewar 32 and the transducer 52, respectively.

The vector C is determined in an initial series of measurements, prior to beginning of magnetic field measurements, wherein the headband 44 is in place, and the transducer 52 is operated at various selected locations on the skull 24 of the subject 26 to map the Ts and Db values at those locations. For these initial measurements, $$C = A_i - B_i,$$

where the subscript i denotes the initial measurement. Thus, there is generated a (Ts,Db,D) mapping of the skull thickness and brain position relative to the headband (or, equivalently and more permanently, relative to the fixed locations on the head such as the nasion and the perauricular points by the technique described in the '355 patent).

The vector V+D is therefore equivalently expressed as $$V + D = O + B + A_i - B_i + D,$$

where B is the vector measured by the positioning system 38 during the course of the magnetic measurements, as described in the '355 patent.

There is an association (Ts,Db,V+D) available for use at any time by the computer 36 in determining brain position and/or skull thickness during real time or post-measurement studies that might be performed on the magnetic field data gathered by the biomagnetometer 20 over a period of time. The availability of this information is important, because it permits fully automated analysis and corrections without dependence upon an assumed model of the skull thickness and brain position, or the need to make separate measurements of the head such as X-ray measurements and then perform tedious cross correlations of positions in different coordinate systems.

Although particular embodiments of the invention have been described in detail for purposes of illustration, various modifications may be made without departing from the spirit and scope of the invention. Accordingly, the invention is not to be limited except as by the appended claims.

What is claimed is:

1. A biomagnetometer that measures a magnetic field produced by a source organ within the body of a subject, comprising:
   means for measuring a magnetic field produced by a source organ, the means for measuring being external to the body and including a magnetic field sensor;
   first position measuring means for measuring the location of the magnetic field sensor relative to the body of the subject, the first position measuring means including a first position sensor;
   means for determining the internal structure of the body relative to the means for determining, the means for determining being external to the body and including a structure-locating sensor;
   second position measuring means for measuring the location of the structure-locating sensor relative to the magnetic field sensor, the second position measuring means including a second position sensor; and
   a computer that controls the means for measuring, the means for determining, the first position measuring means, and the second position measuring means.

2. The biomagnetometer of claim 1, wherein the means for determining includes an ultrasonic transmitter positioned to transmit an ultrasonic wave into the body of the subject.

3. The biomagnetometer of claim 1, wherein the means for determining includes an ultrasonic receiver positioned to receive an ultrasonic wave from within the body of the subject.

4. The biomagnetometer of claim 1, wherein the means for determining includes an ultrasonic transceiver positioned to transmit an ultrasonic wave into the body of the subject and to receive a reflected ultrasonic wave from within the interior of the body of the subject.

5. The biomagnetometer of claim 1, wherein the second position sensor comprises an electromagnetic transmitter and an electromagnetic receiver, one of the transmitter and the receiver being located on the means for determining and the other being located at a known location relative to the means for measuring.

6. The biomagnetometer of claim 1, wherein the means for determining includes ultrasonic means for determining the thickness of the portion of the body lying between a selected location on the surface of the body and the source organ.

7. The biomagnetometer of claim 6, wherein the source organ is the brain and the ultrasonic means measures the thickness of the skull overlying the brain.

8. The biomagnetometer of claim 1, wherein the means for determining includes
   means for measuring the time of flight of a wave from a location external to the body of the subject to internal structure within the body of the subject.

9. A biomagnetometer that measures a magnetic field produced within a body of a subject, comprising:
   means for measuring a magnetic field, the means for measuring being external to a body of a subject;
   ultrasonic means for determining the location of a feature within the body of the subject, the ultrasonic means including means for measuring a time of flight of an ultrasonic wave from a location external to the body to the feature within the body and determining the location of the feature from the time of flight measurement; and means for establishing the position of the ultrasonic means relative to the means for measuring.

10. The biomagnetometer of claim 9, wherein the ultrasonic means includes an ultrasonic transmitter positioned to transmit an ultrasonic wave into the body of the subject.

11. The biomagnetometer of claim 9, wherein the means for establishing includes electromagnetic transmitter/receiver means for establishing the position of the ultrasonic means relative to the means for measuring.

12. The biomagnetometer of claim 11, wherein the electromagnetic transmitter/receiver means includes an electromagnetic transmitter and an electromagnetic receiver, one of the transmitter and the receiver being located on the ultrasonic means and the other being located at a known location relative to the means for measuring.

13. The biomagnetometer of claim 9, further including
a computer that controls the means for measuring and the ultrasonic means.

14. A biomagnetometer that measures a magnetic field produced within a body of a subject, comprising:
means for measuring a magnetic field, the means for measuring being external to a body of a subject;
an ultrasonic transceiver system that transmits an ultrasonic wave into the body of the subject at a selected location on the body and receives a reflected ultrasonic wave from the interior of the body of the subject; and
means for establishing the position of the ultrasonic transceiver system relative to the means for measuring, the means for establishing including
a first position sensor, at least a portion of which is fixed to the body of the subject, and
a second position sensor, at least a portion of which is fixed to the ultrasonic transceiver system.

15. The biomagnetometer of claim 14, wherein at least one of the first and second position sensors includes
electromagnetic transmitter/receiver means for establishing the position of the ultrasonic transceiver system relative to the means for measuring, the electromagnetic transmitter/receiver means including an electromagnetic transmitter and an electromagnetic receiver, one of the transmitter and the receiver being located on the ultrasonic transceiver and the other being located at a known location relative to the means for measuring.

16. The biomagnetometer of claim 14, wherein the means for measuring includes a superconducting quantum interference device that measures a small electrical current.

17. The biomagnetometer of claim 14, wherein the means for measuring includes a pickup coil that produces an electrical current when magnetic flux passes through the pickup coil.

18. The biomagnetometer of claim 14, wherein the ultrasonic transceiver system includes
means for measuring the time of flight of an ultrasonic wave from a location external to the body of the subject to a feature within the body of the subject.

* * * * *